United States Patent [19]

You et al.

[11] Patent Number: 5,224,375
[45] Date of Patent: Jul. 6, 1993

[54] APPARATUS FOR AUTOMATICALLY MEASURING THE VISCOSITY OF A LIQUID

[75] Inventors: Dong-Yong You; Soo-Chang Park; Young-Mann Kwon, all of Kyongi, Rep. of Korea

[73] Assignee: SKC Limited, Kyongi, Rep. of Korea

[21] Appl. No.: 841,420

[22] Filed: Feb. 26, 1992

[30] Foreign Application Priority Data

May 7, 1991 [KR] Rep. of Korea ............... 91-7350

[51] Int. Cl.⁵ ............................................. G01N 11/06
[52] U.S. Cl. ................................................... 73/54.08
[58] Field of Search ............... 73/54.08, 54.07, 54.06, 73/54.05, 54.04

[56] References Cited

U.S. PATENT DOCUMENTS

| 3,604,247 | 9/1971 | Gramain | 73/53.08 |
| 3,895,513 | 7/1975 | Richardson | 73/54.07 |
| 4,616,503 | 10/1986 | Plungis et al. | 73/54.08 |
| 5,142,899 | 9/1992 | Park et al. | 73/54.04 |

FOREIGN PATENT DOCUMENTS

| 81241 | 10/1969 | German Democratic Rep. | 73/54.04 |
| 298135 | 12/1988 | Japan | 73/54.08 |
| 282444 | 11/1989 | Japan | 73/54.07 |

OTHER PUBLICATIONS

Shvestka, M. *Methods of Investigation Automatic Capillary Viscometer* in Polymer Sci. (U.S.S.R.). vol. 16, No. 1 pp. 264–268, 1974.

Kilp, T., et al. *Automatic Capillary Viscometer for the Study of Polymeric Reactions* in Rev. of Sci. Instr. vol. 47, No. 12, pp. 1496–1502, Dec. 1976.

Primary Examiner—Hezron E. Williams
Assistant Examiner—Joseph W. Roskos
Attorney, Agent, or Firm—Thomas J. Dodd

[57] ABSTRACT

An improved apparatus for automatically measuring the viscosity of a sample liquid is disclosed. The apparatus comprises a plurality of viscosimeter tubes mounted in a constant temperature bath, a plurality of vessels adapted for containing the sample liquid, a valve system for controlling the injection and the removal of the sample liquid into and from the viscosimeter tubes and the ascent and descent of the sample liquid in the viscosimeter tubes, a driving circuitry for the valve system, a photosensing device for sensing the meniscus of the liquid at predetermined indication marks of the viscosimeter tubes and a system of measuring the flow time of the sample liquid between two predetermined marks and computing the viscosity of the liquid based on the measured flow time.

13 Claims, 4 Drawing Sheets

APPARATUS FOR AUTOMATICALLY MEASURING THE VISCOSITY OF A LIQUID

BACKGROUND OF THE INVENTION

1. Field of the Invention

The present invention relates to an automatic measuring system of the viscosity of a liquid; and, more particularly, to an apparatus for automatically measuring the viscosity of a liquid, including an automatic control system which can inject a sample liquid into and discharge same from a plurality of viscosimeter tubes.

2. Description of the Prior Art

As is well known in the art, a capillary viscosimeter tube or a vacuum viscosimeter tube is generally used to measure certain lesser viscous liquids. In accordance with the known method of employing viscosimeter tubes, measurement of liquid viscosity is carried out by following the steps of: injecting manually a given volume of sample liquid into a vertical or inclined capillary tube; maintaining the volume of liquid in the tube at a predetermined temperature; measuring the passage time of the volume of liquid between two points of the tube; computing the relative viscosity of the liquid by comparing the passage time of the sample liquid with that of a reference liquid measured under the same condition; and obtaining the absolute and the intrinsic viscosities of the sample liquid based on the measured relative viscosity of the sample and the viscosity of the reference liquid. However, in such typical method of measuring the viscosity of a liquid, the procedure is rather cumbersome due to, e.g., manual introduction of the sample into the tubes and the like.

In addition, there have been provided various viscosimeters for measuring liquid viscosity as known in the art. For example, disclosed in U.S. Pat. No. 3,604,247 is an automatic viscosimeter which comprises a measurement tube, a jacket for containing a transparent liquid therein and maintaining the tube at a constant temperature, means for filling the tube with a sample liquid to be measured, and means for measuring the passage time of the sample between two points.

U.S. Pat. No. 3,713,328 to Choji Aritomi teaches an apparatus for measuring the viscosity of opaque liquids as well as transparent ones, which comprises a viscosimeter having a timing bulb, means for measuring the flow time of the liquid through the timing bulb, means for evacuating the liquid out of the viscosimeter, and means for washing and drying the viscosimeter.

Such viscosimeters as disclosed in the above patents have the disadvantages in that they cannot measure the viscosity of a number of sample liquids at the same time. Further, extra care is required in injecting a sample liquid into the conventional viscosimeter because the liquid is manually supplied to the viscosimeter.

Disclosed in U.S. Pat. No. 3,908,411 is a device for detecting the level of a liquid in a transparent tube, which is suitable for use in capillary tube type viscosimeters.

In U.S. Pat. No. 3,798,966, there is provided a single viscosimeter tube having capillaries of different sizes, which can measure viscosity over a wide range. The measurement task as disclosed in this patent is carried out by a large number of processes; and, therefore, requires a laborious and skillful work. Furthermore, the manufacturing cost of the apparatus is relatively high as it is made in rather complicated structures.

SUMMARY OF THE INVENTION

Accordingly, it is an object of the present invention to provide an apparatus for simultaneously measuring the respective viscosities of a number of sample liquids.

It is another object of the present invention to provide a viscosity measuring apparatus having an automatic control valve system which can inject a sample liquid into and remove same from a plurality of viscosimeter tubes.

It is still another object of the present invention to provide a viscosity measuring apparatus including means for automatically cleaning a plurality of viscosimeter tubes simultaneously.

It is a further object of the invention to provide a viscosity measuring apparatus adapted for employing various sizes of viscosimeter tubes.

It is a still further object of the present invention to provide a viscosity measuring apparatus which can be manufactured at a relatively low cost by simplifying its structures.

The above and other objects of the present invention are accomplished by providing a viscosity measuring apparatus which comprises:

a plurality of viscosimeter tubes mounted in a constant temperature bath;

a plurality of vessels connected to the respective viscosimeter tubes and adapted to contain a sample liquid to be measured;

means for injecting a predetermined amount of the sample liquid into the viscosimeter tubes;

means for moving the sample liquid in the tubes upward and downward;

means for sensing the meniscus of the sample liquid at the marks indicated on the tubes and generating sensing signals;

a valve system for controlling said injecting means and said moving means, respectively;

means for driving the valve system;

means for responding to the signals from said sensing means and controlling said means for driving the valve system; and means for measuring the flow time of the liquid between the two marks and thereby computing the viscosity of the liquid.

Each of the viscosimeter tubes includes a filling tube having a bulb, a measuring tube connected to the bottom portion of the filling tube and having a series of spacedly interconnected upper, middle and lower bulbs and a capillary tube provided between the middle and the lower bulbs, and a branch tube spacedly extending upward from the lower bulb of the measuring tube and arranged in a parallel relationship with each other. The bath is maintained at a predetermined temperature by using a temperature controller.

In addition, each of the viscosimeter tubes is supported by separate frames mounted in the constant temperature bath. Installed at each of the frame are individually slidably upward and downward a plurality of brackets, one of which supports the upper portion of the measuring tube and the remaining ones of which have a pair of corresponding photosensors for sensing the meniscus of the sample liquid. Additionally, each of the sensor brackets includes means for adjusting the distance between the photosensors in order to compensate for the varying dimensions of the viscosimeter tubes to be disposed therebetween.

BRIEF DESCRIPTION OF THE DRAWINGS

The above and other objects and advantages of this invention will be apparent from the following description and accompanying drawings, wherein like numbers refer to like parts in different views.

DETAILED DESCRIPTION OF THE INVENTION

Figure 1:
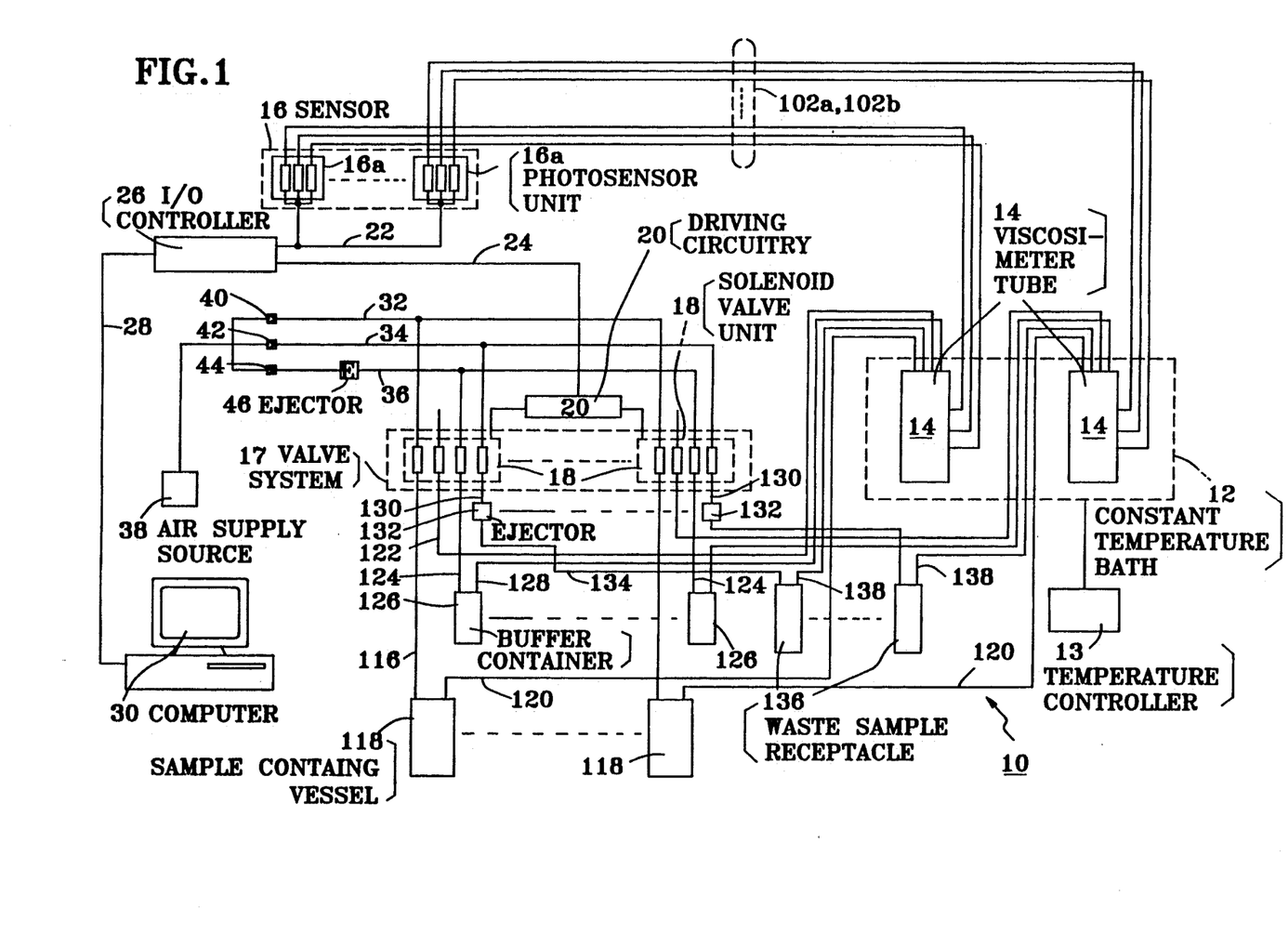
FIG. 1 is a schematic view of a preferred viscosity measuring apparatus in accordance with the invention.

Referring to FIG. 1, there is shown a viscosity measuring apparatus 10 in accordance with a preferred embodiment of the invention, which comprises a plurality of viscosimeter tubes 14 contained in a constant temperature bath 12, a sensor device 16 for detecting the menisci of sample liquids injected into the respective viscosimeter tubes 14, a valve system 17 for controlling the injection and the removal of the sample liquids into and from the viscosimeter tubes 14, a driving circuitry 20 for operating the valve system 17, and an input/output(I/O) controller 26 connected to the sensor device 16 and the driving circuitry 20 through lines 22, 24, respectively.

As is well-known in the art, the bath 12 is used to constantly maintain the samples in the viscosimeter tubes 14 at a predetermined temperature in order to accurately measure the viscosities of the samples. In general, the bath 12 contains a liquid such as water. In addition, depending on the sample liquids to be tested, the temperature of the bath 12 can be adjusted to make the sample liquids attain the required temperature adapted for measuring the viscosities thereof by a temperature controller 13.

The sensor device 16 includes a plurality of photosensor units 16a having a light emitting and a light receiving elements(not shown).

As shown in FIG. 1, the I/O controller 26 is connected to a computer 30 through a line 28. The I/O controller 26 receives signals from the sensor device 16 through the line 22, which detects the menisci of the sample liquids in the viscosimeter tubes 14; feeds them to the computer 30 through the line 28; and supplies control signals from the computer 30 to the driving circuitry 20 through the line 24.

Further, programmed in the computer 30 are the data necessary for measuring the viscosities of the sample liquids, e.g., calculating formula of the intrinsic viscosities of the liquids, correct coefficients of the viscosimeter tubes, concentrations of the liquids, thermal equilibrium time of the liquids within the bath, measuring times of the viscosities of the liquids, washing times of the viscosimeter tubes and the like.

The valve system 17 includes a plurality of solenoid valve units 18 which are connected to a pressurized air supply source 38 through individual air pressure lines 32, 34, 36 as will be more fully described hereinbelow.

As shown in FIG. 1, each of the lines 32, 34 and 36 has air regulators 40, 42, 44 disposed near an entry region of the air supply source 38, respectively, which regulate the pressure of the air to be supplied to sample containing vessels 118 and ejectors 46, 132 to be described hereinbelow. In particular, the air pressure line 36 has the ejector 46 arranged behind the air regulator 44.

Figure 2:
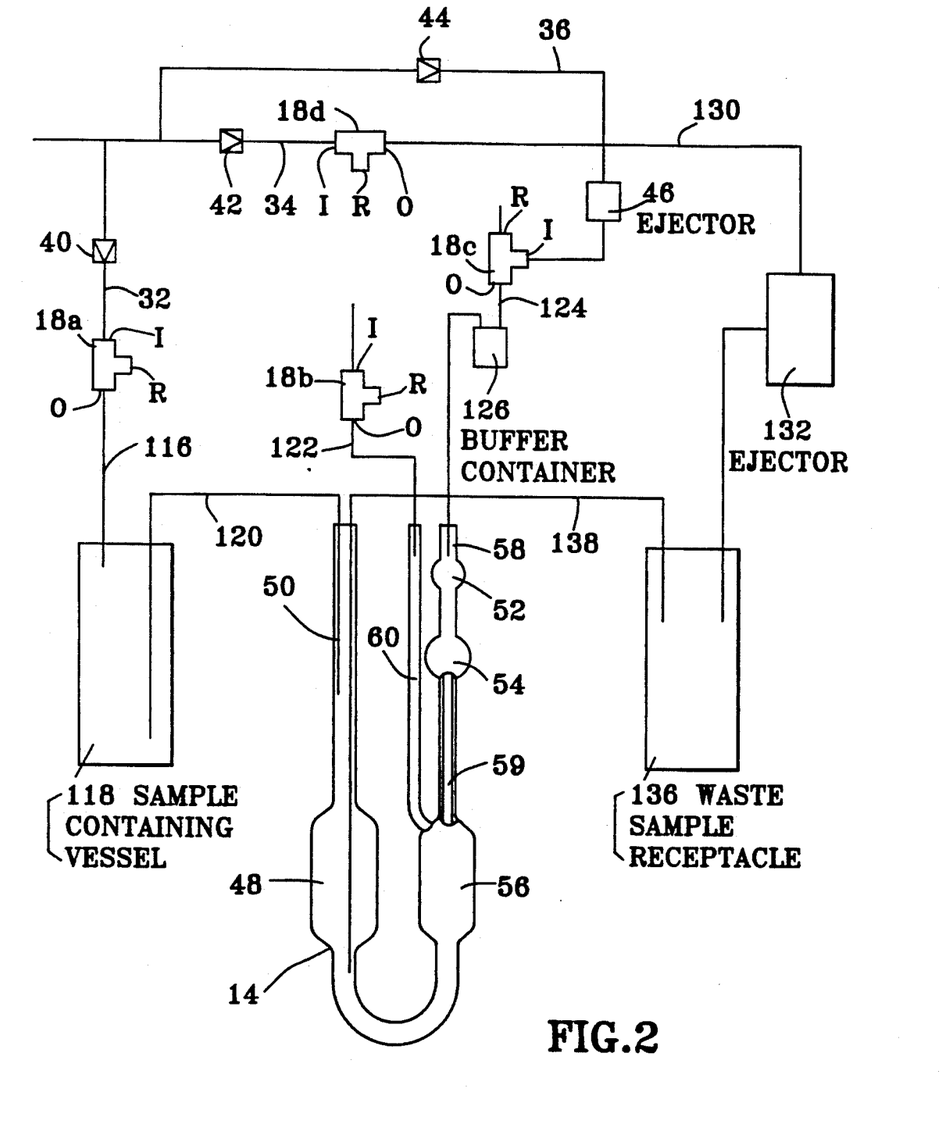
FIG. 2 is a detailed view of one of a plurality of valve units for controlling the injection and the removal of a sample liquid into and from a plurality of viscosimeter tubes.
Figure 3:
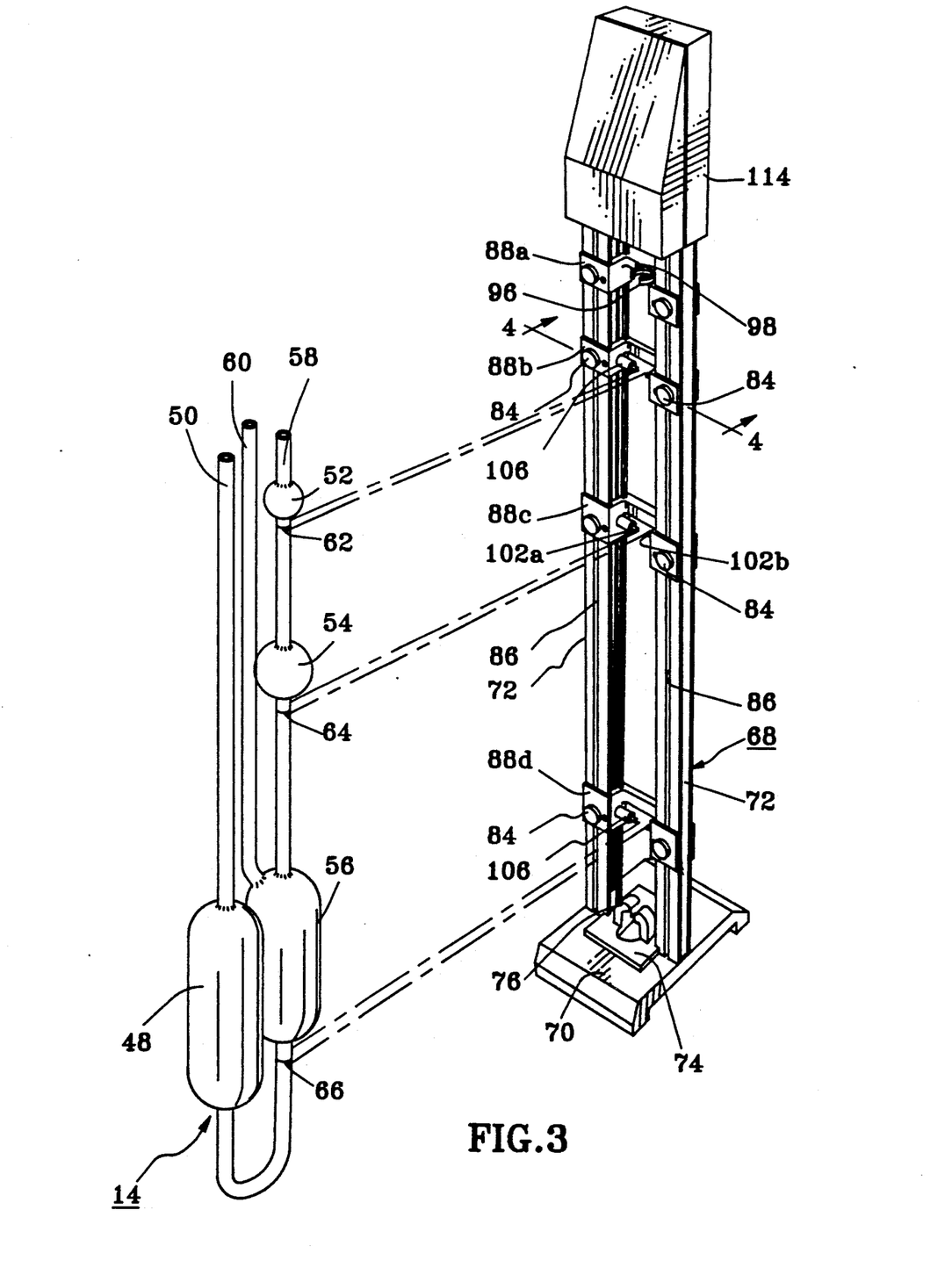
FIG. 3 is a detailed view of a viscosimeter tube and a frame supporting the viscosimeter tube therein in accordance with a preferred embodiment of the invention.

The viscosimeter tube 14 in accordance with a preferred embodiment of the invention is shown in the left side of FIG. 3. The viscosimeter tube 14 comprises a filling tube 50 having a bulb 48 at the lower portion thereof, a measuring tube 58 connected to the bottom portion of the filling tube 50 in a bending configuration, e.g., a U-shape and having a series of spacedly interconnected upper, middle and lower bulbs 52, 54, 56 and a capillary tube 59(see FIG. 2) provided between the middle and the lower bulbs 54, 56, and a branch tube 60 spacedly extending upward from the lower bulb 56 of the measuring tube 58. The respective tubes 50, 58 and 60 are generally arranged in a parallel relationship with each other.

Provided above and below the middle bulb 54 of the measuring tube 58 are an upper and a middle indication marks 62, 64 which are used to measure the passage time of the liquid therebetween. Also, as will be described hereinbelow, provided on or below the lower bulb 56 of the measuring tube 58 is at least a lower indication mark 66 which may be useful for injecting the required amount of the sample into the viscosimeter tube 14. Otherwise, the lower indication mark 66 may be provided on the bulb 48 of the filling tube 50.

In the right side of FIG. 3, there is shown a frame 68 adapted for supporting the viscosimeter tube 14 therein in accordance with a preferred embodiment of the invention. The supporting frame 68 comprises a base 70, a pair of oppositely spaced vertical columns 72 secured on the base 70 and a pedestal 74 mounted on the base 70 and disposed between the two vertical columns 72. The pedestal 74 has a U-shaped groove 76 designed which is adapted to receive the bottom portion of the viscosimeter tube 14 therein.

Figure 4:
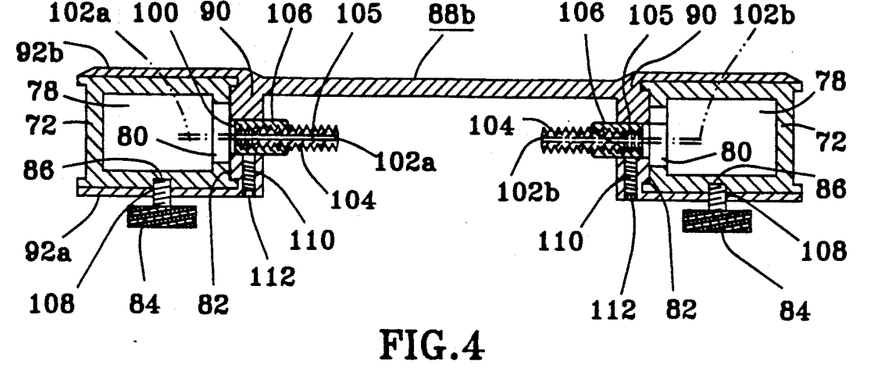
FIG. 4 is a sectional view taken along line 4—4 of FIG. 3.

As best shown in FIG. 4, each of the columns 72 includes an elongated vertical bore 78 and a relatively narrow channel 80 communicating with the bore 78. In addition, provided at the inside of the respective columns 72 are respective stepped guide portions 82. Also, formed at the front surface of the respective columns 72 are elongated vertical guide slots 86 arranged in a parallel relationship, which are engaged with bolts 84(see FIG. 3).

Figure 5:
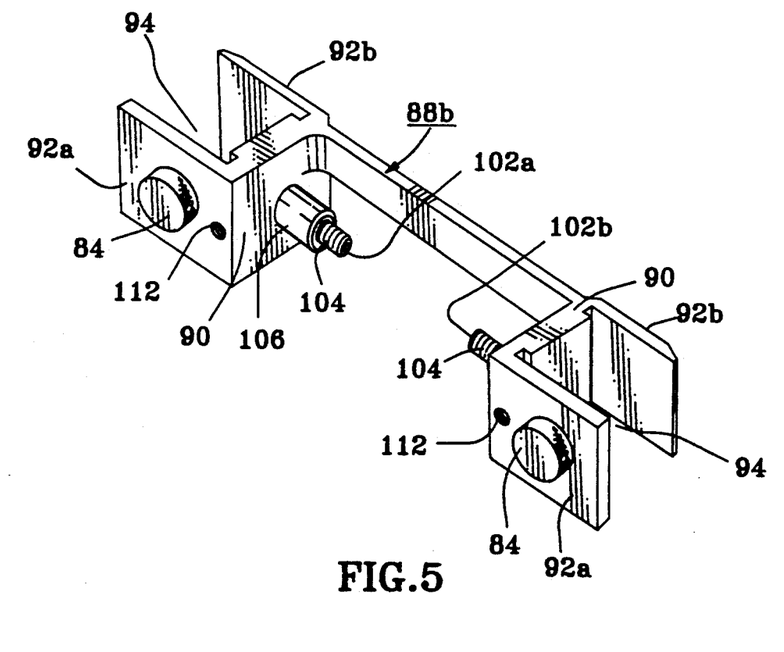
FIG. 5 is a perspective view of one of sensor brackets slidably mounted on the frame shown in FIG. 3.

Turning back to FIG. 3, there are a plurality of separate brackets 88a, 88b, 88c, 88d slidably mounted on the columns 72 in upward and downward directions. The bracket 88a which supports the upper portion of the measuring tube 58 is disposed above the remaining brackets 88b, 88c, 88d having corresponding optical fiber cables 102a, 102b arranged therein(see FIG. 4), respectively which are capable of detecting the meniscus of the sample liquid at the indication marks 62, 64, 66 of the measuring tube 58 as will be described hereinbelow. With reference to FIGS. 3, 4, and 5, the respective brackets 88a, 88b, 88c, 88d include supporting portions 90 slidably engaged with the stepped guide portions 82 of the columns 72 and front and back flanges 92a, 92b extending outward from the ends of the supporting portions 90 in a perpendicular relationship. Therefore, the front and the back flanges 92a, 92b associated with the supporting portions 90 can form spaces 94 capable of accommodating the columns 72, respectively (see FIG. 5).

As illustrated in FIG. 3, attached at the middle region of the uppermost bracket 88a is an elastic piece 98 having a groove 96 which is adapted to receive and support the upper portion of the measuring tube 58 therein.

As best shown in FIGS. 3 and 4, each of the sensor brackets 88b, 88c, 88d has a hollow 100 formed in the supporting portion 90, which communicates with the channel 80 of the column 72 and which is arranged in a substantially perpendicular relation relative to the channel 80. A holder 106 is slidably inserted into each of the hollows 100 of the respective supporting portions 90. A diameter of the holder 106 is preferably smaller than the width of the channel 80 so that the holder 106 easily passes through the channel 80 in the adjustment of the distance between the optical fiber cables 102a, 102b to compensate the various sizes of the viscosimeter tubes 14 as will be more fuly described hereinbelow. Further, engaged in the holders 106 are screw bolts 104 having through-holes 105 suitable for accommodating the optical fiber cables 102a, 102b therein.

The respective optical fiber cables 102a, 102b are connected to the light emitting and the light receiving elements(not shown) in each of the photosensor units 16a(see FIG. 1) through the bore 78 and the channel 80 of the column 72 as shown in FIG. 4.

As best shown in FIGS. 4 and 5, provided in the front flange 92a of the respective brackets 88a, 88b, 88c, 88d are threaded holes 108 engaged with the bolts 84 which secure the brackets to the column 72 at a required position. In addition, formed in the supporting portion 90 of the sensor brackets 88b, 88c, 88d are threaded holes 112 engaged with set screws 110 which are provided to fix tightly the holder 106 to the hollow 100 at a proper position.

In accordance with the preferred embodiment of the invention, variously sized viscosimeter tubes which are designed to be suitable for measuring different liquids can be employed. In this connection, for example, although each of the indication marks 62, 64, 66 is variously located on the measuring tube 58 depending on the size of the viscosimeter tube, the optical fiber cables 102a, 102b can be easily adjusted to correspond to the individual indication marks 62, 64, 66 because the respective sensor brackets 88b, 88c, 88d having the optical fiber cables arranged therein are separately movable upward and downward on the column 72 and are secured thereon at the positions opposite to the marks by the bolts 84.

Moreover, the distance between the respective corresponding optical fiber cables 102a, 102b is readily adjusted to compensate for the variations in the diameter of the measuring tube 58 by moving the holder 106 in the hollow 100 in the forward and backward directions and then fastening same at a required location by the set screw 110.

Therefore, maintenance of a substantially constant interval between the optical fiber cables 102a, 102b and the measuring tube 58 enables the sensor device 16 to sense more accurately the meniscus of the sample liquid. The set screw 110 can be rotated by an appropriate tool(not shown).

The individual column 72 has a case 114 mounted on the upper portion thereof, which houses the sensor device 16 therein.

Returning to FIGS. 1 and 2, the respective solenoid valve units 18 consist of four solenoid valves 18a, 18b, 18c, 18d which are 3-way valves, respectively. One of the measuring systems and solenoid valve units will be described for the sake of convenience.

The solenoid valves 18a, 18b, 18c, 18d are selectively energized or de-energized by the driving circuitry 20 controlled by the computer 30. The first solenoid valve 18a is connected to the first air pressure line 32 and also to the vessel 118 via a line 116, which is adapted to contain the sample liquid. The sample liquid contained in the vessel 118 is supplied to the filling tube 50 via a supply line 120.

As will be described hereinbelow, one port of the second solenoid valve 18b is always closed and another port thereof is connected to the branch tube 60 via a line 122, while the remaining one thereof opens at the atmospheric pressure when the second valve 18b is de-energized.

The third solenoid valve 18c is connected to the third air pressure line 36 and also to a buffer container 126 via a line 124. In addition, the buffer container 126 is connected to the measuring tube 58 via a line 128. The buffer container 126 serves to accept and deposit an overflow liquid from the measuring tube 58 therein which may be produced by an erroneous operation of the sensor device 16, thereby preventing the overflow liquid from flooding the third solenoid valve 18c and the ejector 46.

The fourth solenoid valve 18d is connected to the second air pressure line 34 and to an ejector 132 via a line 130. Additionally, the ejector 132 is connected to a waste sample receptacle 136 via a line 134. The waste receptacle 136 is connected to the filling tube 50 via a drainage line 138. As best shown in FIG. 2, one end of the drainage line 138 extends adjacent to the bottom portion of the filling tube 50.

In FIG. 2, one of the solenoid valve units 18 in accordance with a preferred embodiment of the invention is depicted in detail. As previously described, each of the respective solenoid valves 18a, 18b, 18c, 18d has three ports. Each of the ports R of the valves opens at the atmospheric pressure when the respective valves are de-energized. The ports I of the first and the fourth solenoid valves 18a, 18d are connected to the first and the second air pressure lines 32, 34, respectively, and the ports O thereof are connected to the lines 116, 130 of the sample containing vessel 118 and the ejector 132, respectively. As previously described, the port I of the second solenoid valve 18b is always closed and the port O thereof is connected to the line 122 of the branch tube 60. The port I of the third solenoid valve 18c is connected to the ejector 46 and the port O thereof to the line 124 of the buffer container 126.

In accordance with a preferred embodiment of the invention, the procedure of measuring the viscosity of a sample liquid will be now described hereinbelow, with reference to the accompanying drawings. It should be understood that some or all of the viscosimeter tubes 14 are selectively or concurrently used to measure the viscosity of the sample liquid. In this connection, one of the representative measuring systems is described herein for the sake of convenience. The computer 30 employed in the present invention is programmed so as to appropriately carry out the measuring and the washing operations.

Prior to the measurement of the viscosity of the sample, the viscosimeter tube 14 selected is mounted in the frame 68. And then, the respective pairs of optical fiber cables 102a, 102b are positioned to correspond to the indication marks 62, 64, 66 of the measuring tube 58 by an individual movement of the sensor brackets 88b, 88c, 88d on the columns 72. Thereafter, the frame 68 is placed in the bath 12.

In the next step, after the sample liquid has been supplied to the vessel 118, the driving circuitry 20 will be operated through the I/O controller 26 by the manipulation of the computer 30. Since the respective solenoid valves 18a, 18b, 18c, 18d are de-energized at the initial stage, the ports O and R thereof communicate each other and the ports I thereof are closed. Therefore, the viscosimeter tube 14, the sample containing vessel 118 and the waste receptacle 136 are put under the atmospheric pressure.

At this stage, only the first solenoid valve 18a is energized by the driving circuitry 20. Thus, the port R of the first valve is closed and the ports I and O thereof communicate with each other. Therefore, the air pressure is applied to the vessel 118 from the air pressure source 38 via the first valve 18a and the line 116. As a result of the application of the air pressure to the vessel 118, the sample liquid contained in the vessel 118 is fed into the filling tube 50 via the line 120. When the sample liquid reaches the lower indication mark 66 of the measuring tube 58, the sensor device 16 senses the meniscus of the sample liquid at the lower mark 66 by means of the lower optical fiber cables 102a, 102b and generates a signal to be supplied to the computer 30 through the I/O controller 26. Once the computer 30 receives the signal from the sensor device 16, it supplies a control signal to the driving circuitry 20 through the I/O controller 26. If the first solenoid valve 18a is de-energized by the driving circuitry 20, its port I is closed while its port R is opened at the atmospheric pressure. As a result of the de-energization of the first valve 18a, the air supply to the vessel 118 is shut off. Thus feeding of the sample liquid into the viscosimeter tube 14 is immediately stopped. Therefore, the viscosimeter tube 14 is filled with the required amount of the sample.

Thereafter, the sample in the viscosimeter tube 14 is maintained at a predetermined temperature within the bath 12 before the measurement of the sample is commenced.

When the sample reaches the predetermined temperature, the second and the third solenoid valves 18b, 18c are energized by the driving circuitry 20. Therefore, the ports R of the second and the third solenoid valves 18b, 18c are closed while the ports I and O thereof communicate with each other. Accordingly, the air pressure is supplied to the ejector 46 through the third air pressure line 36, which functions to produce the vacuum in the measuring tube 58. Thus, the sample liquid is moved upward by the production of the vacuum in the measuring tube 58. The sample continues to ascend until it reaches a point immediately above the upper indication mark 62 of the measuring tube 58 through the capillary tube 59 as programmed. If the sample liquid reaches the upper indication mark 62, the sensor device 16 senses the meniscus of the sample at the upper mark 62 by means of the upper optical fiber cables 102a, 102b and generates a signal which is applied to the computer 30 through the I/O controller 26.

Once the computer 30 receives the signal from the sensor device 16, it provides a control signal for de-energizing the second and the third solenoid valves 18b, 18c with the driving circuitry 20 through the I/O controller 26. The ports R of the second and the third valves 18b, 18c are opened at the atmospheric pressure while the ports I thereof are closed, by the de-energization of the second and the third valves 18b, 18c. Therefore, the ascending operation of the sample is stopped because the vacuum is not applied to the measuring tube 58. In addition, the atmospheric pressure is given to the filling tube 50, the measuring tube 58 and the branch tube 60. Consequently, the sample liquid flows downward by gravity.

When the sample liquid passes through the upper and the middle indication marks 62, 64, the sensor device 16 detects the meniscus of the sample liquid at the upper and the middle marks 62, and generates signals to be sent to the computer 30. The computer 30 receives the signals from the sensor device 16 through the I/O controller 26 and measures the flow time of the meniscus of the sample liquid between the upper anthe middle marks 62, 64. As described above, the computer also calculates the viscosity of the sample based on the flow time; and may print out the measured results by a printer(not shown) in a conventional manner. One measurement of the viscosity of the sample is completed through the steps as described above.

If required, the sample may be repeatedly measured before the tested sample is removed from the viscosimeter tube 14.

After the measurement of the sample is completed, the tested sample is discharged from the viscosimeter tube 14 to the waste receptacle 136 as described hereinbelow.

Upon the completion of sample measurement, the viscosimeter tube 14 and the waste receptacle 136 are put under the atmospheric pressure as previously described. At this time, in order to remove the tested sample from the viscosimeter tube 14, the fourth solenoid valve 18d is energized by the driving circuitry 20 and, thereby, the ports I and O thereof communicate with each other. Thus, the air pressure is supplied to the ejector 132 via the second air pressure line 34 from the source 38. Accordingly, since the vacuum is produced in the waste receptacle 136 by the operation of the ejector 132, the tested sample contained in the viscosimeter tube 14 is sucked in the waste receptacle 136 via the drainage line 138.

After the drainage of the tested sample, it is preferable to have the viscosimeter tube 14 cleaned so as to prepare for the measurement of a next sample liquid.

The washing process is substantially similar to the measuring one. The vessel 118 is filled with a washing agent after the evacuation of the sample liquid therefrom. In some cases, e.g., if the sample contains a solvent component, the tested sample itself may be used as the washing liquid before it is removed from the viscosimeter tube 14. In the first washing step, the ports I and O of the first solenoid valve 18a communicate with each other while the ports I of the remaining solenoid valves 18b, 18c, 18d are closed, by the operation of the driving circuitry 20. Therefore, the air pressure is supplied to the vessel 118 through the lines 32, 116 and, thereby, the washing liquid contained in the vessel 118 is injected into the filling tube 50 via the line 120 by the operation of the air pressure.

As previously described, once the washing liquid reaches the lower indication mark 66 of the measuring tube 58, the sensor device 16 senses the meniscus of the washing liquid and generates a signal which is sent to the computer 30 through the I/O controller 26. Thereafter, the computer 30 sends a control signal to the driving circuitry 20 through the I/O controller 26, which de-energizes the first solenoid valve 18a. Consequently, the port I of the first valve 18a is closed and the injection of the washing liquid into the viscosimeter tube 14 is stopped at the same time. Subsequently, the third solenoid valve 18c is energized by the driving circuitry 20 and, thereby, its port I is opened. Hence, the air pressure is supplid to the ejector 46 through the third air pressure line 36. As described above, the vacuum produced in the measuring tube 58 by the operation of the ejector 46 causes the washing liquid to move upward. When the washing liquid reaches the upper indication mark 62 of the measuring tube 58, the sensor device 16 senses the meniscus of the washing liquid at that mark 62 and sends the signal to the computer 30 through the I/O controller 26. And then, the driving circuitry 20 receives a controlsignal from the computer 30 and de-energizes the third solenoid valve 18c whose port I is closed. Thus, as described above, the vacuum is not produced in the measuring tube 58 and, thereby, the ascending operation of the washing liquid is stopped. In addition, the atmospheric pressure is applied to the viscosimeter tube 14. Consequently, the washing liquid flows downward by gravity and washes the inside of the viscosimeter tube 14.

If required, the viscosimeter tube 14 may be repeatedly washed by using the washing liquid injected thereinto. In this case, such washing operations are achieved by repeatedly ascending and descending the washing liquid in the measuring tube 58 in the same manner as described above.

After the washing operation, the washing liquid is discharged from the viscosimeter tube 14 in the same way as the sample liquid is discharged in the measurement procedure.

Although this invention has been shown and described with respect to the preferred embodiments, it will be understood by those skilled in the art that certain changes and modifications may be made without departing from the spirit and scope of the invention as defined in the following claims.

What is claimed is:

1. An apparatus for measuring the viscosity of a liquid which comprises:
    a plurality of viscosimeter tubes mounted in a constant temperature bath, each of said viscosimeter tubes including a filling tube, a measuring tube connected to a bottom portion of the filling tube and having a series of spacedly interconnected upper, middle and lower bulbs and a capillary tube provided between the middle and the lower bulbs, and a branch tube extending upward from the lower bulb of the measuring tube, wherein the filling, the measuring and the branch tubes are arranged in a substantially parallel relationship with each other, with upper and middle indication marks being located above and below the middle bulb and a lower indication mark located on or below the lower bulb;
    a plurality of vessels connected to said respective filling tubes via supply lines and adapted to contain a sample liquid;
    means for injecting the sample liquid contained in the vessels into said respective measuring tubes;
    means for moving the sample liquid upward and downward in said measuring tubes;
    a valve system for controlling said injection means a said moving means, said control valve system including a plurality of valve units each including a group of first, second, third and fourth solenoid valves, wherein the first solenoid valves are connected to a first air pressure line and to said respective sample containing vessels, the second solenoid valves are connected to said respective branch tubes, the third solenoid valves are connected to a third air pressure line having a first ejector thereon and to said respective measuring tubes through individual buffer containers, and the fourth solenoid valves are connected to a second air pressure line and to lines having second ejectors connected to respective waste receptacles;
    means for driving said control valve system;
    means for sensing the meniscus of the sample liquid at said respective indication marks of said measuring tubes and generating sensing signals;
    means for responding to the sensing signals and controlling said driving means for operating the valve system;
    means for receiving the sensing signals, measuring the flow time of the sample liquid between said upper and middle indication marks of said measuring tubes and computing the viscosity of the sample liquid based on the measured flow time; and
    means for discharging the sample liquid from said respective viscosimeter tubes, said discharging means being controlled by said control valve system.

2. The apparatus of claim 1, wherein said respective solenoid valves are selectively operated by said driving means.

3. The apparatus of claim 1, wherein said respective air pressure lines are connected to an air pressure source.

4. The apparatus of claim 3, wherein each of said respective air pressure lines has an air regulator at an entry region of the air.

5. An apparatus for measuring the viscosity of a liquid which comprises:
    a plurality of viscosimeter tubes mounted in a constant temperature bath, each of said viscosimeter tubes including a filling tube, a measuring tube connected to a bottom portion of the filling tube and having a series of spacedly interconnected upper, middle and lower bulbs and a capillary tube provided between the middle and the lower bulbs, and a branch tube extending upward from the lower bulb of the measuring tube, wherein the filling, the measuring and the branch tubes are arranged in a substantially parallel relationship with each other, with upper and middle indication marks being located above and below the middle bulb and a lower indication mark located on or below the lower bulb;
    a plurality of vessels connected to said respective filling tubes via supply lines and adapted to contain a sample liquid;
    means for injecting the sample liquid contained in the vessels into said respective measuring tubes;
    means for moving the sample liquid upward and downward in said measuring tubes;
    a valve system for controlling said injection means and said moving means;
    means for driving said control valve system;
    means for sensing the meniscus of the sample liquid at said respective indication marks of said measuring tubes and generating sensing signals;

means for responding to the sensing signals and controlling said driving means for operating the valve system;

means for receiving the sensing signals, measuring the flow time of the sample liquid between said upper and middle indication marks of said measuring tubes and computing the viscosity of the sample liquid based on the measured flow time; and a plurality of frames adapted to separably secure said respective viscosimeter tubes thereto and mounted in the constant temperature bath;

each of said respective frames having a base, a pair of columns spacedly fixed to the base, a pedestal mounted on the base and having a U-shaped groove suitable for accommodating the bottom portion of said viscosimeter tube therein and a plurality of separately positioned sets of brackets slidably secured to said columns.

6. The apparatus of claim 5, wherein each of the uppermost brackets has an elastic piece having a groove caple of receiving an upper portion of said measuring tube, while each of the remaining brackets has a pair of light emitting and receiving optical fiber cables connected to said sensing means and arranged therein.

7. The apparatus of claim 6, wherein each of the columns has means for individually adjusting each of said brackets so that each pair of said optical fiber cables corresponds to said respective indication marks and so that said elastic piece supports the upper portion of said measuring tube.

8. The apparatus of claim 7, wherein said adjusting means includes a pair of vertical guide slots provided on a side of each column in a parallel relationship with each other, and bolts engaged with said guide slots through threaded holes formed in each of said brackets.

9. The apparatus of claim 8, wherein each of said columns includes an elongated vertical bore formed therein, an elongated vertical channel communicating with said bore and a stepped guide portion disposed adjacent to the channel.

10. The apparatus of claim 9, wherein each of said brackets includes a supporting portion slidably engaged with the stepped guide portion of each column.

11. The apparatus of claim 10, wherein each of said supporting portions of said remaining brackets includes means for individually adjusting the distance between the corresponding optical fiber cables.

12. The apparatus of claim 11, wherein said distance adjusting means includes a hollow communicating with said channel in a perpendicular relationship, a holder slidably engaged with the hollow and set screw for securing and releasing the holder to and from the hollow.

13. The apparatus of claim 12, wherein each of said optical fiber cables is inserted into a through-hole of a screw bolt threadedly engaged with the holder.

* * * * *